United States Patent [19]

Maeda et al.

[11] Patent Number: 4,782,113

[45] Date of Patent: * Nov. 1, 1988

[54] NEOCARZINOSTATIN DERIVATIVES AND METHOD OF PRODUCING THE SAME

[75] Inventors: Hiroshi Maeda, 631-3, Aza-Tamukae, Hotakubohon-Machi, Kumamoto City, Kumamoto Pref.; Ryunosuke Kanamaru; Nakao Ishida, both of Sendai; Toshihiko Yoshitake, Kurashiki; Minoru Ueda, Okayama, all of Japan

[73] Assignees: Kuraray Co., Ltd., Kurashiki; Yamanouchi Pharmaceutical Co., Ltd.; Kayaku Antibiotics Research Co., Ltd., both of Tokyo; Hiroshi Maeda, Kumamoto, all of Japan

[*] Notice: The portion of the term of this patent subsequent to Mar. 22, 2005 has been disclaimed.

[21] Appl. No.: 911,454

[22] Filed: Sep. 25, 1986

Related U.S. Application Data

[63] Continuation of Ser. No. 751,977, Jun. 28, 1985, abandoned, which is a continuation of Ser. No. 636,490, Aug. 1, 1984, abandoned.

[30] Foreign Application Priority Data

Aug. 8, 1983 [JP] Japan ................................. 58-145418

[51] Int. Cl.$^4$ ........................ A61K 31/785; C08F 8/32
[52] U.S. Cl. ..................................... 525/54.1; 424/78; 260/DIG. 47
[58] Field of Search .................... 525/54.1, 54.11, 328; 526/272, 238.1; 424/78; 260/DIG. 47

[56] References Cited

U.S. PATENT DOCUMENTS

| | | | |
|---|---|---|---|
| 3,085,994 | 4/1963 | Muskat | 526/272 |
| 3,121,043 | 2/1964 | Tobin et al. | 525/327.6 |
| 3,245,933 | 4/1966 | Muskat | 526/272 |
| 4,182,752 | 1/1980 | Maeda et al. | 260/DIG. 47 |

Primary Examiner—John Kight
Assistant Examiner—Nathan M. Nutter
Attorney, Agent, or Firm—Burns, Doane, Swecker & Mathis

[57] ABSTRACT

Substantially pure neocarzinostatin anticancer agents have the formula (A):

(SMA)—(NCS)—(SMA)        (A)

wherein (NCS) is a divalent neocarzinostatin residue and (SMA) comprises the monovalent residue of a partially half-esterified styrene-maleic acid copolymer having a weight-average molecular weight of from 800 to 2,500, said (NCS) residue being bonded to said (SMA) residues via amide linkages formed between primary amino groups of the neocarzinostatin molecule and carbonyl groups of the partially half-esterified styrene-maleic acid copolymer.

24 Claims, 10 Drawing Sheets

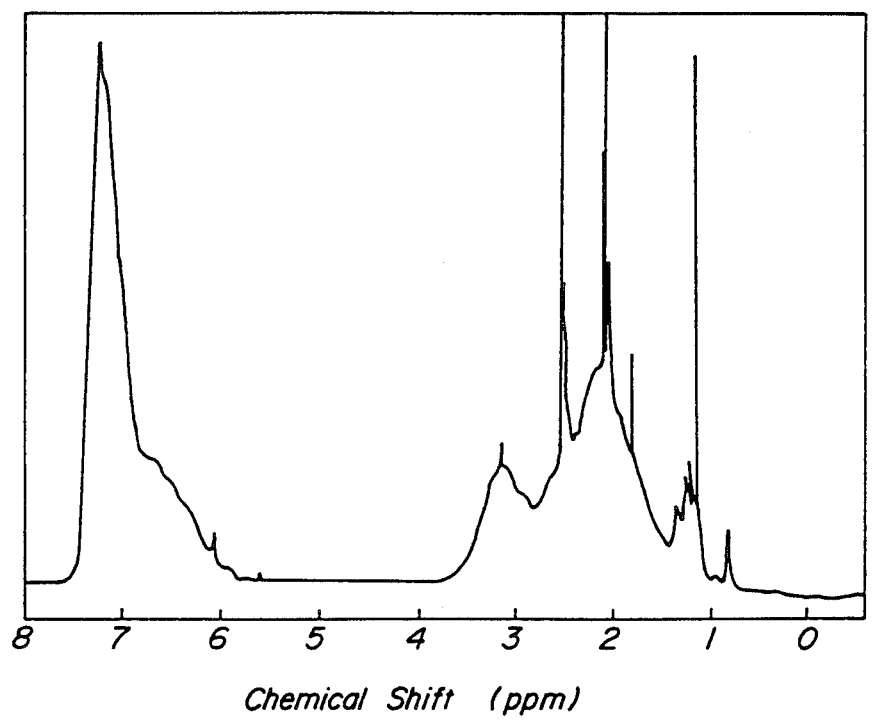
FIG_1

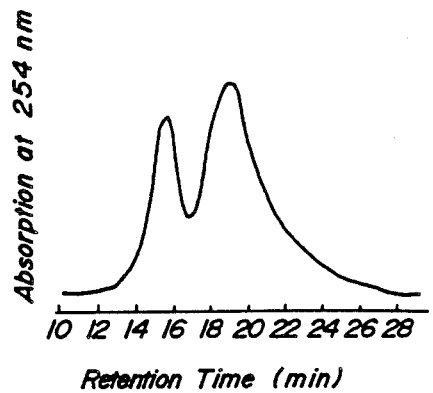
FIG_2a
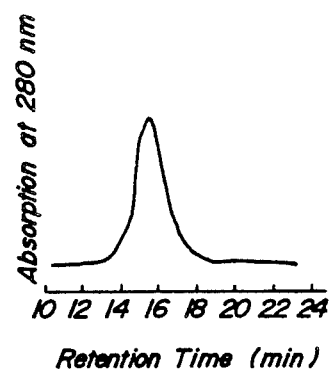
FIG_2b
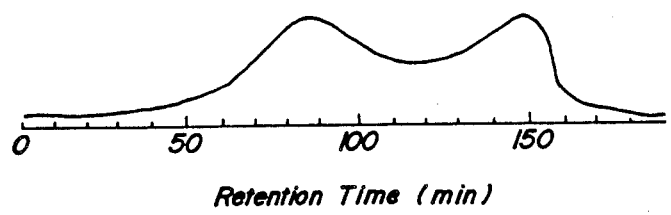
FIG_3

FIG_4c
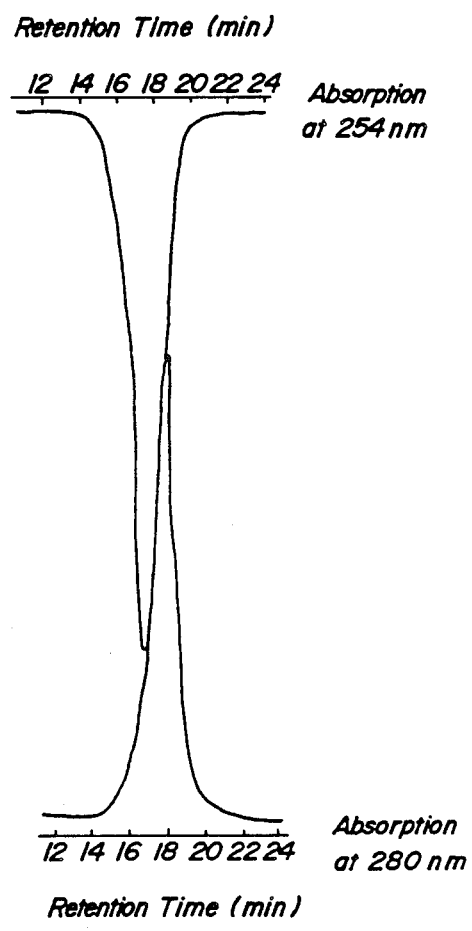
FIG_4d
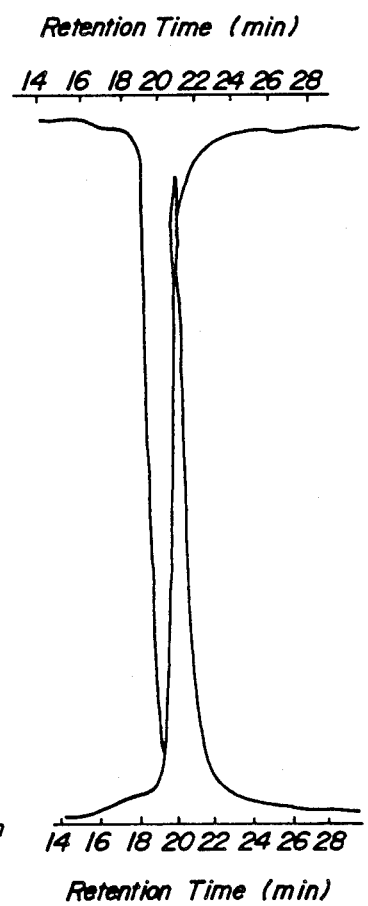

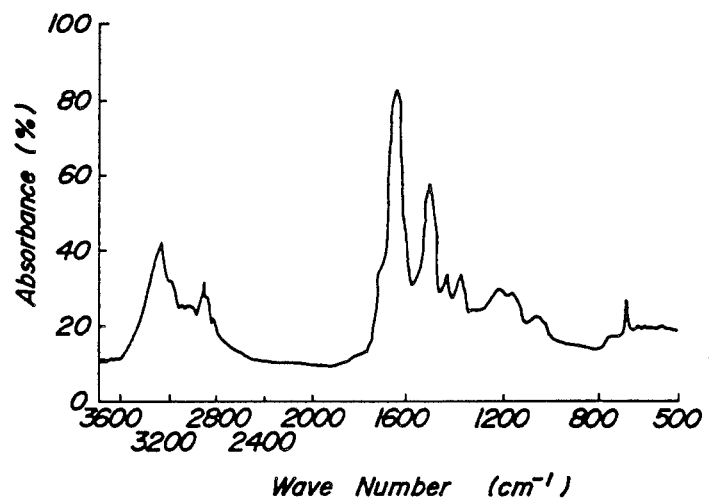
FIG_5a
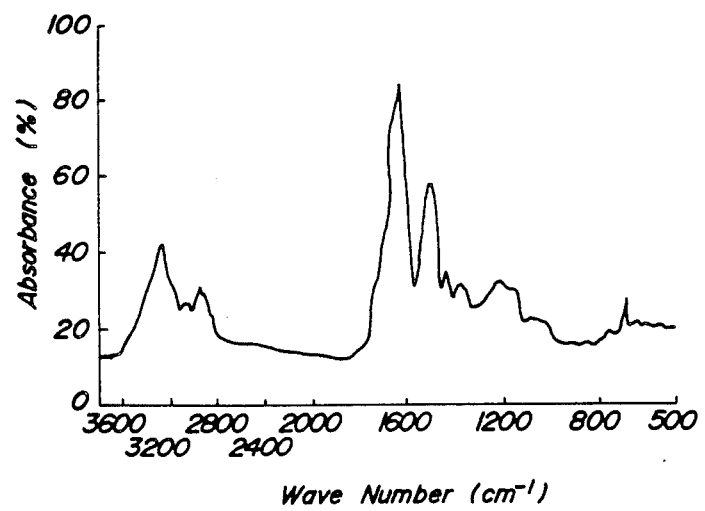
FIG_5b

FIG_5c
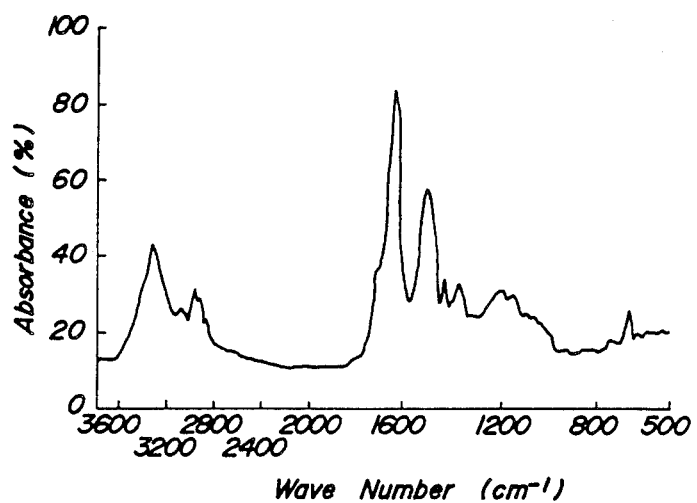
FIG_5d
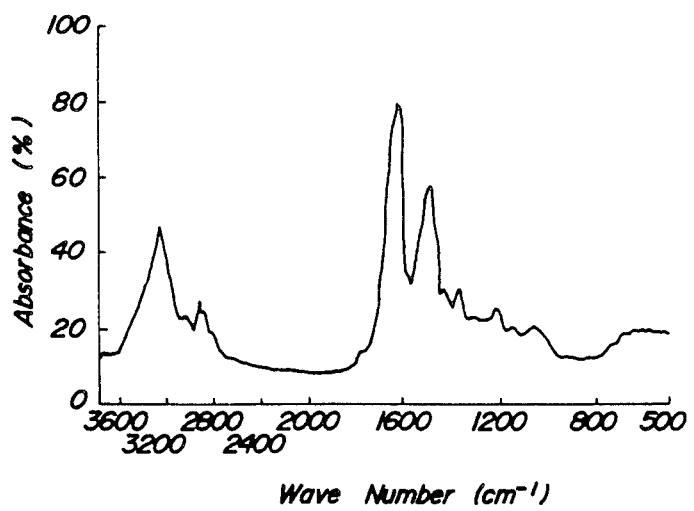

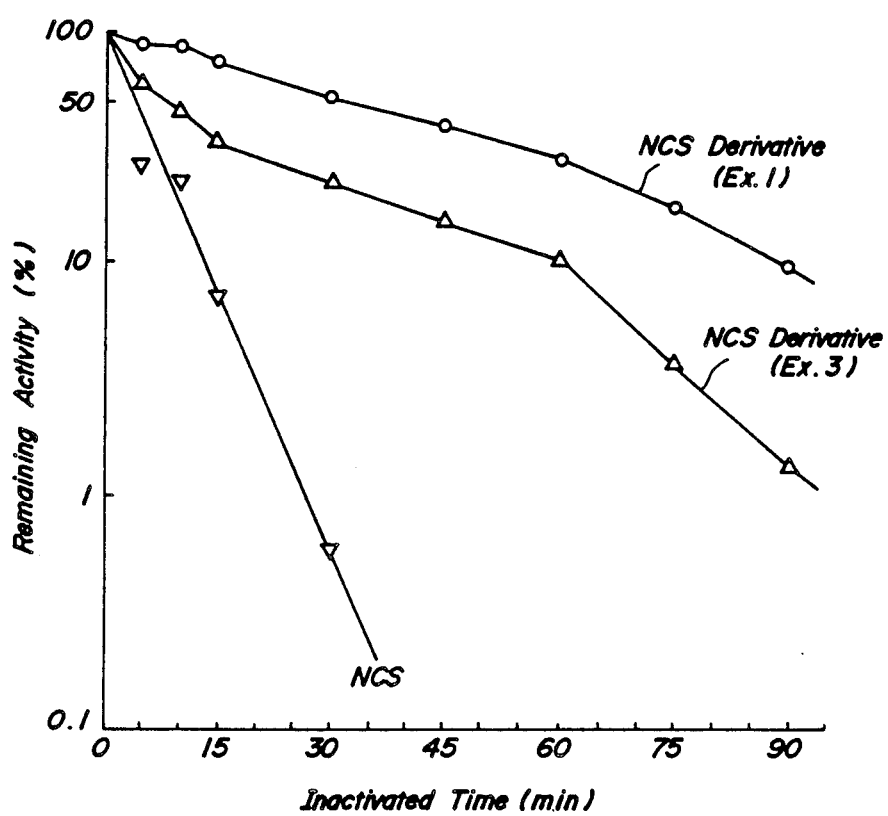
FIG_7

NEOCARZINOSTATIN DERIVATIVES AND METHOD OF PRODUCING THE SAME

This application is a continuation of application Ser. No. 751,977, filed June 28, 1985 and now abandoned, which is a continuation of now abandoned U.S. Ser. No. 636,490 of Aug. 1, 1984.

BACKGROUND OF THE INVENTION

1. Field of the Invention

The present invention relates to novel compounds of neocarzinostatin derivatives having excellent anticancer activity, which have the following formula

(SMA)—(NCS)—(SMA)   (I)

wherein (NCS) represents divalent neocarzinostatin residue in which one hydrogen atom is removed from each of the primary amino group in alanine residue at the N-terminal of neocarzinostatin and that in lysine residue at 20th position from the N-terminal of neocarzinostatin and (SMA) represents monovalent partially half-esterified styrene-maleic acid copolymeric residue having a weight-average molecular weight of 800~2,500 and consisting of structural units of styrene residue

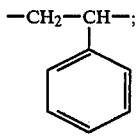

half-esterified maleic acid residue

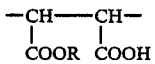

wherein R is an alcohol residue wherein hydroxyl group is removed from an alkanol having 1–4 carbon atoms, ethylene glycol monoalkyl ether in which the alkyl group has 1–2 carbon atoms or glycerine dialkyl ether wherein the alkyl group has 1–2 carbon atoms; and maleic acid residue

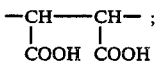

and a residue having the following formula in which a hydroxyl group of one carboxyl group in maleic acid residue is removed and linked to be bonded to the neocarzinostatin residue

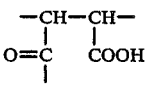

wherein the linkage of carbon atom in carbonyl group bonds to the neocarzinostatin residue, and a method for producing the same.

2. Description of the Prior Arts

Neocarzinostatin (abbreviated as "NCS" hereinafter) is a proteinaceous anticancer agent produced in a medium in which *Streptomyces carzinostaticus* var. F-41 Kuroya is cultured (Japanese Patent Publication No. 42 (1967)-21,752 and U.S. Pat. No. 3,334,022). With respect to the primary structure of this substance, the total number of amino acid residues and estimated molecular weight have been reported to be 109 and 10,700 respectively, by Hiroshi Maeda who is one of the present inventors (Science, 178, 875–876 (1972) and Arch. Biochem. Biophys., 163, 379–385).

In the treatment of cancer, the metastasis of cancer cells is important and particularly the metastasis of said cells into lymphatic system is the most important problem. A wide variety of neocarzinostatin derivatives have been examined with the aim of lowering the toxicity, prolonging the biological activity of the drug in vivo, and directing its delivery more to the lymphatic system. As a result, it has been found that neocarzinostatin derivatives having the following formula (II), which is obtained by reacting two primary amino groups present in the molecule of neocarzinostatin with a partially hydrolyzed styrene-maleic anhydride copolymer, possess the above described activities and this has been disclosed in U.S. Pat. No. 4,182,752,

(SMA')—(NCS)—(SMA')   (II)

wherein (NCS) means the same NCS residue as in the above described formula (I) and (SMA') means styrene maleic acid copolymeric residue having an average molecular weight of 2,500~80,000, in which one of the pendant carboxylic groups forms acid amide linkage with a primary amino group in NCS molecule.

But, the above described NCS derivatives are soluble in an aqueous medium and may be applied to intravenous administration but are poor in lipid solubility. The inventors have made various studies for improving the affinity to the tumor by giving both the water and lipid solubility to neocarzinostatin and found that NCS composites shown by the following formula (III)

(NCS')—(SMA")$_n$   (III)

wherein (NCS') represents NCS residue, (SMA") represents partially half-esterified styrene-maleic acid copolymeric residue having an average molecular weight of 1,000~10,000 and the subscript n is an integer of 1~35, which are produced by reacting NCS with a partially half-esterified styrene-maleic anhydride copolymer (abbreviated as "E-SMA" hereinafter), have higher affinity to the tumor than NCS derivatives shown by the above described formula (II) and therefore can develop more excellent anticancer activity, and further have excellent water and lipid solubility, so that these NCS composites may be applied in both the forms of the aqueous and the oily compositions and filed with respect to such composites as U.S. patent application Ser. No. 469,235, now pending as Ser. No. 06/730,823, filed May 6, 1985, Canadian Patent Application No. 422,497 and European Patent Application No. 83301027.5.

However, such NCS composites may have a variety of numerical values within a range of n from 1 to 35 but the composites practically produced as the examples have been ones in which the n value is 5 or more. When the biological assay based on the growth inhibition of *Sarcina lutea* (abbreviated as "biological assay" hereinafter) which has been known to be parallel to the antitumor activity (reported by N. Ishida, K. Miyazaki, K. Kumagai and M. Rikimaru, J. Antibiot (Tokyo), Serial A 18, 68 (1965) is examined with respect to such composites, it has been found that the activity of NCS composites is about 1/10 as compared with that of NCS and said composites are insufficient for the intraarterial administration in which a dose is limited. The reason of such a low biological activity is presumably ascribed to the very high content of the partially half-esterified styrene-maleic acid copolymeric residue to exhibit the biological activity based on NCS residue.

SUMMARY OF THE INVENTION

In order to obtain NCS derivatives with high biological activities, the inventors have intensively studied the reaction of NCS with partially half-esterified styrene-maleic anhydride copolymer and found that the reaction product of NCS and E-SMA, in which two molecules of E-SMA are bonded to one molecule of NCS through formation of acid amide linkages, is isolated from such a reaction mixture and the present invention has been accomplished.

Thus, the first aspect of the present invention lies in NCS derivatives shown by the above described formula (I).

The above described NCS derivatives (I) can be isolated only by reacting NCS with a specific E-SMA to a high degree of reaction and then subjecting the reaction product to gel filtration.

That is, the second aspect of the present invention lies in a method for producing NCS derivatives shown by the above described formula (I), which comprises reacting neocarzinostatin in an aqueous medium with a large molar excess of powdery E-SMA consisting of structural units of styrene residue

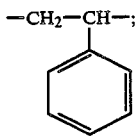

half-esterified maleic acid residue

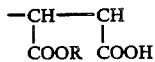

wherein R is an alcohol residue wherein hydroxyl group is removed from an alkanol having 1~4 carbon atoms, ethylene glycol monoalkyl ether in which the alkyl group has 1~2 carbon atoms, or glycerine dialkyl ether in which the alkyl group has 1~2 carbon atoms; and maleic anhydride residue

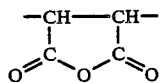

said E-SMA satisfying the following formulae (IV) and (V)

$$800 \leq \overline{Mw} \leq 2,500 \qquad (IV)$$

$$\overline{Mw}/\overline{Mn} \leq 1.5 - 1.1 \times 10^{-4}\overline{Mw} \qquad (V)$$

wherein $\overline{Mw}$ means a weight-average molecular weight of E-SMA and equation (IV) is allowed to have any $\overline{Mw}$ from 800 to 2,500, and $\overline{Mn}$ means a number-average molecular weight of E-SMA, and subjecting the reactio product to gel filtration to isolate the NCS derivative which conforms to the above described formula (I). When NCS is reacted with an E-SMA in an aqueous medium, solution after the completion of the reaction includes, other than NCS derivative of the present invention, partially half-esterified styrene-maleic acid copolymer produced by ring-opening hydrolysis of the maleic anhydride ring portion of E-SMA (referred to as "ring-opening hydrolyzed product of E-SMA" hereinafter), unreacted NCS, an intermediate product to the NCS derivative conforming to the above described formula (I) which have the following formula (VI)

$$(NCS'')—(SMA) \qquad (VI)$$

wherein (NCS'') represents monovalent NCS residue in which one hydrogen atom is removed from one of the two primary amino groups at the N-terminal and at the 20th position from the N-terminal of NCS, and (SMA) has the same meaning as in the formula (I), and by-products having the following formulae (VII), (VIII) and (IX)

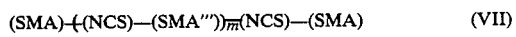
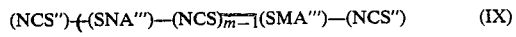

wherein (NCS) has the same meaning as in the formula (I), (NCS'') has the same meaning as in the formula (VI), (SMA) has the same meaning as in the formula (I), and (SMA''') represents bivalent partially half-esterified styrene-maleic acid copolymeric residue comprising styrene residue, half-esterified maleic acid residue, maleic acid residue and two residues, each having a formula in which hydroxyl group is removed from one carboxyl group in maleic acid residue and bonded to NCS residue and m represents 1 or 2. Among these unreacted products and by-products, particularly the unreacted NCS, the ring-opening hydrolyzed product of E-SMA and the intermediate product shown by the formula (VI) cause problem in the separation of NCS derivatives of the present invention. As mentioned hereinafter, the inventors have succeeded in the isolation of NCS derivatives (I) by the following means. That is, by reacting NCS in the reaction system to a high degree of reaction by using a large molar excess of E-SMA based on NCS, the presence of the unreacted NCS and the intermediate product (VI) can be minimized and by using E-SMA having the limited molecular weight and molecular weight distribution, the separation of the NCS derivatives (I) thus formed and the ring-opening hydrolyzed product of E-SMA through the gel filtration is made easy, whereby the present invention has succeeded in the isolation of NCS derivatives (I). The present invention can provide substantially pure NCS derivatives, so that these derivatives can be practically applied for drug.

The NCS derivatives (I) of the present invention surprisingly show high biological activity comparable to NCS. Such an NCS derivative is soluble in aqueous buffer above pH 6.5 and can be stably dispersed in lipid, such as Lipiodol (Ethiodol) (made by Laboratoires André Guerbet (Paris, France), Lipiodol Ultra-Fluid: Fatty acid ethyl ester of iodized poppy seed oil, iodine content: 38 W/W) or the like, to prepare a lipid soluble composition and therefore can be applied through various means, such as intravenous, intraarterial, subcutaneous, intramuscular, intraperitoneal oral administration and the like. In particular, in the intraarterial administration of the lipid injection, the dose per injection is very small and it is required only infrequently but the enough activity can be retained by the derivatives of the present invention having high activities. Since this oily injection possesses iodine, its diagnostic value under X-ray is extremely useful. (Iwai, K., Konno, T. and Maeda, H: Cancer Research vol. 44 2115, 1984).

BRIEF DESCRIPTION OF THE DRAWINGS

FIG. 1 is an example of NMR spectrum of a styrene-maleic anhydride copolymer before fractionation, which is used in the production of NCS derivatives according to the present invention;

FIGS. 2a and 2b are examples of gel permeation chromatography (GPC) after dialysis of a reaction product of NCS with an E-SMA;

FIG. 3 is an example of a gel filtration profile of such a reaction product;

FIGS. 4a, 4b and 4c are examples of GPC of the NCS derivatives according to the present invention;

FIG. 4d is an example of GPC of NCS which is a starting material of the NCS derivatives according to the present invention;

FIGS. 5a, 5b and 5c are examples of infrared (IR) spectra of the NCS derivatives according to the present invention;

FIG. 5d is an example of IR spectrum of NCS which is a starting material of the NCS derivatives according to the present invention;

FIG. 7 is a graph showing the inactivation of the biological activity of the NCS derivatives according to the present invention and NCS which is a starting material thereof.

DESCRIPTION OF THE PREFERRED EMBODIMENTS

Figure 4A:
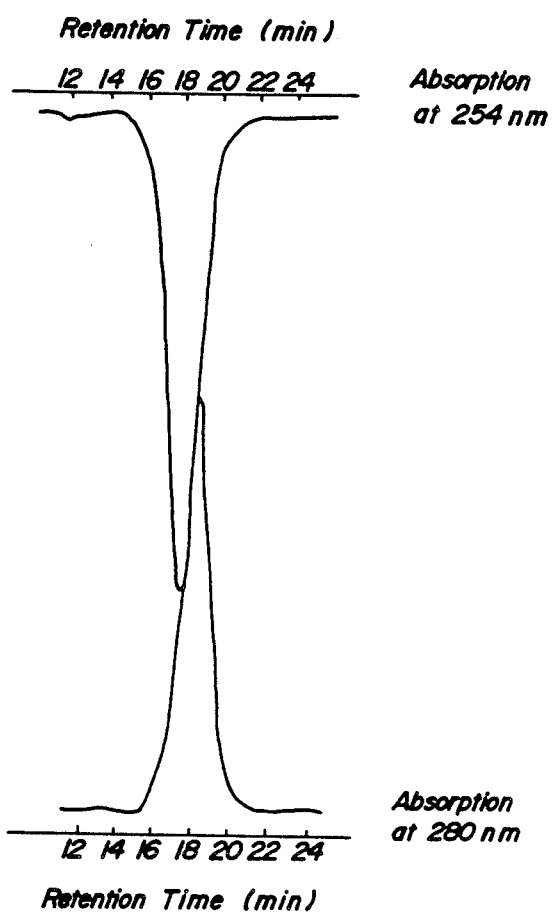

Detailed explanation will be made with respect to the present invention.

Firstly, explanation is made with respect to the structure of the NCS derivatives (I). The NCS derivatives (I) are formed by bonding one NCS residue with two partially half-esterified styrene-maleic acid copolymeric residues through acid amide linkages. The NCS residue is a protein having two primary amino groups, one at N-terminal alanine (at position 1) and lysine group at the position 20th from the N-terminal as disclosed in the above described literature [Science, 178, 875~876 (1972)]. An NCS molecule contains a large number of functional groups, such as hydroxyl groups and secondary amino groups other than two primary amino groups but in the NCS derivatives of the present invention, the functional groups other than two primary amino groups do not substantially serve to form chemical bond with the partially half-esterified styrene-maleic acid copolymeric residue. Namely, the NCS residue which is one of the structural components of the NCS derivatives of the present invention has such a form that one hydrogen atom is removed from each of the above described two primary amino groups in NCS, that is, in total, two hydrogen atoms are removed to form two acid amide-linkages.

The partially half-esterified styrene-maleic acid copolymeric residue, which is another structural component in the NCS derivatives of the present invention, consists of the structural units of (a) styrene residue

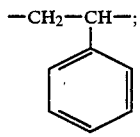

(b) half-esterified maleic acid residue

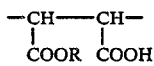

wherein R is an alcohol residue in which hydroxyl group is removed from an alkanol having 1-4 carbon atoms, ethylene glycol monoalkyl ether in which the alkyl group has 1-2 carbon atoms or glycerine dialkyl ether in which the alkyl group has 1-2 carbon atoms;

(c) maleic acid residue

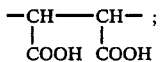

and (d) a residue having the following formula in which a hydroxyl group of one carboxyl group in maleic acid residue is removed and linked to be bonded to the neocarzinostatin residue

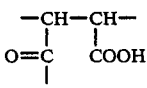

wherein the linkage of carbon atom of carbonyl group bonds to NCS residue. Such a copolymeric residue is obtained from E-SMA applied for preparing the NCS derivatives of the present invention. In the above described copolymeric residue, the residue (d) is formed through the reaction of maleic anhydride residue

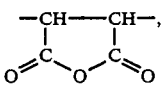

with the primary amino group in NCS and the residue (c) is formed through hydrolysis of maleic anhydride residue not reacted with NCS in E-SMA in an aqueous medium. The residues (a) and (b) correspond to styrene residue and half-esterified maleic acid residue in E-SMA, respectively. The ratio of these residues (a), (b), (c) and (d) varies depending upon selection of the polymer composition of E-SMA, because E-SMA is selected in view of the reactivity with NCS as mentioned hereinafter but the E-SMA subjected to the reaction with NCS consists of many molecular species differing in both molecular weight and chemical composition and as a result, there is distribution with respect to the ratio of the residues (a), (b), (c) and (d), (but one residue (d) is always in such copolymeric residue). For example, when each molecule of E-SMA is subjected to the reaction with NCS, the partially half-esterified styrene-maleic acid copolymeric residue formed by reacting E-SMA having only one maleic anhydride residue with NCS molecule has no maleic acid residue. However, the E-SMA subjected to the reaction with NCS has the composition distribution as mentioned above, so that E-SMA molecule containing two or more maleic anhydride residues is concurrently present and when such a molecule reacts with NCS molecule, the partially half-esterified styrene-maleic acid copolymeric residue having one or more maleic acid residues is formed. Accordingly, the copolymeric residue thus formed has distribution in the molecular weight and the composing ratio of the respective composing residue as in the case of E-SMA, so that the presence of these composing residues should be considered on the average as a whole. Even when E-SMA having a small average number of maleic anhydride residue is used as the starting material, E-SMA molecules having two or more maleic anhydride residues are present, so that when the partially half-esterified styrene-maleic acid copolymeric residue in the NCS derivatives formed is observed on an average, maleic acid residue is always contained as the structural unit even if the average content of said residue is less than one. As a consequence, the residues other than residue (d) in such a copolymeric residue as a whole should be expressed as average values so that cannot be in integers.

Then, a comment will be made with respect to the average molecular weight of the partially half-esterified styrene-maleic acid copolymeric residue portion in the NCS derivatives of the present invention. Said average molecular weight is important to be 800~2,500 on weight-average. Such an average molecular weight can be determined by the manner disclosed in the examples mentioned hereinafter and the NCS derivatives having the copolymeric residue having an average molecular weight of greater than 2,500 are difficult in the separation from the reaction product as mentioned below, the NCS derivatives having the copolymeric residue wherein the weight-average molecular weight is less than 800 are difficultly used in practice.

In the production of the NCS derivatives of the present invention, the selection of the E-SMA subjected to the reaction with NCS is important and explanation will be made with respect to this point. As mentioned above, E-SMA consists of styrene residue (a'), half-esterified maleic acid residue (b') and maleic anhydride residue (c'). The molar ratio of the residue (a') to the sum of the residue (b') and the residue (c') in E-SMA is preferred to be substantially about 1:1~1.3:1, more preferably about 1:1. Such composing ratio is mainly selected in view of the solubility of the E-SMA into an aqueous medium when E-SMA is reacted with NCS while being dissolved in the aqueous medium. The higher the ratio of the residue (a') to the sum of the residue (b') and (c') in E-SMA, the lower the solubility of E-SMA in the aqueous medium. It is practically impossible to obtain E-SMA having the ratio of the residue (a') being smaller than 1 in the copolymerization of styrene with maleic anyhydride.

Concerning the ratio of the residue (b') to the residue (c'), by taking both the solubility of E-SMA in an aqueous medium and the reactivity of NCS in the reaction of E-SMA with NCS into consideration, the ratio (the ratio of maleic anhydride ring) of the residue (c') to the sum of the residue (b') and the residue (c') is preferred to be 15~16 mol% (in the half-esterified ratio, 35~85 mol%), more preferably 20~60 mol%. The E-SMA wherein such content of maleic anhydride ring is less than 15 mol% is insufficient for the reactivity with NCS and thus it is impossible to attain sufficiently high degree of reaction of the two primary amino groups in NCS. On the other hand, if the degree of half-esterification ratio is less than 35 mol%, the content of carboxyl group is too low to be soluble into aqueous reaction medium, so that the reaction does not take place spontaneously.

Concerning the residue (b') in the E-SMA subjected to NCS, the presence of the residue (b') is important in the following points. By giving the half-esterified maleic acid residue (b) in the NCS derivatives of the product of the present invention [formula (I)], the affinity of the NCS derivatives to tumor is improved. However, if the alcohol residue in the residue (b') has too large number of carbon atoms, the solubility of the E-SMA in an aqueous medium becomes poor and such an alcohol residue is not preferable. The residue (b') in E-SMA is introduced by reacting styrene-maleic anhydride copolymer with an alcohol to add the alcohol molecule to a part of maleic anhydride residues and open the ring; the alcohols to give the ester in the residue (b') are methanol, ethanol, n-propyl alcohol, isopropyl alcohol, n-butyl alcohol, isobutyl alcohol, sec-butyl alcohol and tert.-butyl alcohol as alkanols having 1–4 carbon atoms, 2-methoxyethanol and 2-ethoxyethanol as etheyleneglycol monoalkyl ether having 1–2 carbon atoms; 2,3-dimethoxy-1-propanol, 2-ethoxy-3-methoxy-1-propanol, 3-ethoxy-2-methoxy-1-propanol, 2,3-diethoxypropanol, 1,3-dimethoxy-2-propanol, 1-ethoxy-3-methoxy-2-propanol and 1,3-diethoxy-2-propanol as glycerine dialkyl ethers, as shown with respect to the structure of the partially half-esterified styrene-maleic acid copolymeric residue in the above mentioned NCS derivatives.

In addition to the above described conditions on the constitution of E-SMA as the starting material of the present invention, the average molecular weight and the molecular weight distribution of the E-SMA must be within the ranges shown by the above described formulae (IV) and (V).

The formula (IV) corresponds to the average molecular weight range of the partially half-esterified styrene-maleic acid copolymeric residue portion resulting from E-SMA in the already defined NCS derivatives. The E-SMA has the molecular weight distribution and thus the species of E-SMA having higher molecular weights in such a distribution may be adequately high in the reactivity with NCS because the average content of maleic anhydride residue, at which the reaction takes place with NCS, is higher and the probability is high and the probability to form the partially half-esterified styrene-maleic acid copolymeric residue in the NCS derivative after reaction with NCS is also higher. Consequently, in a strict sense, the weight-average molecular weight of the E-SMA and the average molecular weight of the copolymeric residue in the NCS derivates thus formed are different in exactness and the value of the latter tends to be more or less higher than that of the former. However, as seen from the examples mentioned hereinafter, this difference is not so high and it is permissible to consider that the weight average molecular wieght of E-SMA is substantially equivalent to the average molecular weight of the partially half-esterified styrene-maleic acid copolymeric residue.

For the production of the NCS derivatives of the present invention, it is important to use E-SMA having a weight average molecular weight of less than 2,500 and the specifically narrow molecular weight distribution shown by the formula (V). The NCS derivatives of the present invention elute more faster than the hydrolyzed and ring-opened product of E-SMA in the gel filtration but these substances tend to elute simultaneously to a considerable extent. However, when E-SMA in which the average molecular weight and the molecular weight distribution have been adjusted as described above, is used for the reaction with NCS, the molecular size of the ring-opening hydrolyzed product of E-SMA is smaller than that of the NCS derivatives (I) present in the reaction liquid, so that the difference of the elution time of these components in the gel filtration is satisfactorily high and the breadths of the molecular weight distribution of these components are considerably narrow. Consequently, the separability of these components in the gel filtration becomes high and the isolation of the NCS derivatives (I) becomes easier.

In the production of the NCS derivatives of the present invention, the above mentioned E-SMA is used but the constitution of the partially half-esterified styrene-maleic acid copolymeric residue of the NCS derivatives thus formed depends upon the E-SMA applied for the reaction. Such E-SMA is obtained by partially half-esterification of styrene-maleic anhydride copolymer (abbreviated as "SMA" hereinafter). However, SMA produced under the usual polymerization conditions has broad molecular weight distribution with the molecular weight distribution index ($\overline{M}w/\overline{M}n$) being about 2.0 or more.

The E-SMA obtained by partial half-esterification of such an SMA also maintains such a broad molecular weight distribution, so that even if E-SMA is reacted with NCS, it is difficult to isolate the NCS derivatives (I) from the reaction product through gel filtration (see Comparative Example 2 described hereinafter). Therefore, it is necessary to refine the molecular weight distribution by effecting fractionation either before or after partial esterification of conventional SMA having a broad molecular weight distribution obtained by the usual polymerization (for example, styrene and maleic anhydride are subjected to a solution polymerization at a temperature of 90°~200° C. in a solvent (cumene, p-cymene, ethylbenzene, etc.) having a function as a chain transfer agent by using benzoyl peroxide, dicumyl peroxide, etc. as an initiator according to Japanese Patent Publication No. 47(1972)-44,552 and U.S. Pat. No. 3,245,933). As the fractionating process, use may be made of solubility process or ultrafiltration process and the like, but the most preferable one comprises fractionating SMA through fractional solution process and partially half-esterifying the obtained SMA having a narrow molecular weight distribution to convert SMA into E-SMA. In such a partial half-esterification reaction of SMA, the degree of esterification depends upon the kind and amount (molar ratio based on SMA) of alcohol used.

Thus obtained E-SMA is reacted with NCS in an aqueous medium. As seen from the structural formula (I) of NCS derivatives, it is merely necessary to react two molecules of E-SMA per one molecule of NCS, so that the ideal amount of E-SMA required is 2 moles based on 1 mole of NCS. But, in reality, as mentioned above, maleic anhydride residue portion in E-SMA reacts competitively with the primary amino group, hydroxyl group in NCS molecule and water molecule and some other functional residues in NCS molecule. Some of the reaction products thus formed are hydrolyzed to yield maleic acid residue. Some of the anhydride residue in E-SMA are hydrolyzed in the reaction condition and its ring is opened and converted into partially half-esterified styrene-maleic acid copolymer without reacting with NCS. When the ring of the anhydride is opened, the products can react no longer with NCS. Thus, E-SMA must be used in large excess of the theoretical molar ratio with respect to NCS. Since the weight average molecular weight of E-SMA is 800~2,500 as shown by the formula (IV) and the molecular weight of NCS is 10,700, even though the amount of E-SMA used varies depending upon the average molecular weight, said amount must be more than 0.15 part by weight in the case of E-SMA having a weight average molecular weight of 800 and 0.47 part by weight in the case of E-SMA having a weight average molecular weight of 2,500. In particular, when the average molecular weight of E-SMA is small or the content of maleic anhydride residue is low, the average number of maleic anhydride residue contained per one molecule is small and such E-SMA is high in the ratio of E-SMA molecule having no maleic anhydride residue (having no reactivity with NCS), so that it is important to use a large molar excess of E-SMA. In order to increase the extent or reaction of primary amino groups in NCS with E-SMA to a sufficiently high level, it is preferred to use 2–15 parts by weight and more preferably 3–12 parts by weight of E-SMA based on 1 part by weight of NCS, although the amount of E-SMA required to achieve the above condition depends upon the average molecular weight and structure of the E-SMA as described above. When the amount of E-SMA used is more than 15 parts by weight based on 1 part by weight of NCS, the reaction product in a reaction mixture is diluted so much by the ring-opening hydrolyzed product of E-SMA that in the subsequent separation will be poor and thus such an amount of E-SMA is not feasible and the use of such a large amount is inpractical.

Furthermore, in the reaction of NCS with E-SMA, the total concentration of NCS and E-SMA in the reaction solution is preferred to be 10~35% by weight and more preferably 15~32% by weight. When the total concentration in the reaction solution is lower than 10% by weight, the rate of reaction of NCS with E-SMA is low and the chance where maleic anhydride residue in E-SMA is hydrolyzed is increased, causing a difficulty in obtaining the desired derivative of NCS. Conversely, when the total concentration of NCS and E-SMA exceeds 35% by weight, the viscosity of the reaction solution is so high that the stirring of the reaction mixture becomes difficult and such a condition is not desirable.

The reaction of NCS with E-SMA is generally effected by firstly dissolving NCS in an aqueous sodium bicarbonate, sodium acetate, ammonium bicarbonate and the like and then adding stepwise powdery E-SMA to this solution. The concentration of these salts is not specifically defined but it is preferable to maintain the pH of the reaction mixture always at 7.5–9.5, preferably 8.0–8.7. When pH of the solution is lower than 7.5, E-SMA is insoluble or difficulty soluble in the aqueous solution and it is impossible to obtain the sufficient concentration to perform the reaction with NCS or a very long time is needed for the dissolution and such a pH is not practicable. When pH of the reaction solution is higher than 9.5, it is possible that the biological activity of the NCS derivatives in the solution decreases and such pH also is thus undesirable. Furthermore, in order to maintain the biological activity of the NCS derivatives, it is preferable to react at a temperature lower than 15° C. in the dark.

By selecting the above described reaction conditions appropriately, the conversion of the primary amino group in NCS in the reaction of NCS with E-SMA can exceed as high as more than 90 mol%, in most case more than 95 mol%. When such a high conversion is attained, unreacted NCS is practically undetectable and an amount of the intermediate product shown by the formula (VI) which is formed by reacting only one of the two primary amino groups of NCS with E-SMA is very low. On the other hand, although the increase of the by-products shown by the formulae (VII), (VIII) and (IX) is expected to increase in parallel with the increase in the degree of conversion of the primary amino group of NCS, it has been found that the amount of these by-products are unexpected low and the yield of the object product of the present invention is very high. These by-products can be separated during purification mentioned hereinafter.

Then, the NCS derivatives of the present invention are isolated from the reaction mixture by the gel filtration method. The substrate to be used in the gel filtration is selected from ones having an exclusion limit as expressed in the molecular weight 50,000~150,000, preferably 60,000~100,000 for globular proteins and the most preferable substrate to obtain the NCS derivatives (I) of the present invention can be selected from the following commercially available gel particles; Sephadex G-50, G-75, G-100 (made by Pharmacia Fine Chemicals AB, Uppsala, Sweden) and Bio-Gel P-60, P-100 (made by Bio-Rad Laboratories, U.S.A.). Other desirable gel filtration conditions may be arbitrarily selected. In order to carry out the gel filtration efficiently, it is preferable to perform the purification of the reaction solution after completion of reaction of NCS with E-SMA by dialysis or ultrafiltration by means of a dialysis tube or an ultra-filtration membrane in which the cut-off molecular weight of the globular protein is about 10,000, to remove the salt and concurrently partially remove the ring-opening hydrolyzed product of E-SMA which remained unreacted with NCS. Alternatively, the NCS derivatives of the present invention may be isolated by subjecting the reaction solution to a preliminary purification through a gel filtration and then to an additional gel filtration.

The NCS derivatives (I) of the present invention are separated from the other reaction products during the above described gel filtration. Then, the eluate cut containing the NCS derivatives (I) is subjected to lyophilization to remove the solvent, whereby NCS derivatives (I) of the present invention are isolated. It has been identified by the various experiments shown in the following examples that the thus isolated substance has the structure of the formula (I).

The NCS derivatives (I) of the present invention can be utilized as medicaments in human therapy by local administration, such as the primary site of cancer and the area of tumor removal or resection, or by intracutaneous, subcutaneous, intramuscular, intravenous, intraarterial and oral administration, or by external application, such as applying or spraying to local site to be treated, suppository, intravesical instillation. The dose regimen depends on administration routes, malignancy stage and grade of tumor, types of tumor, and various conditions of patients. Further, the dosages depends on the purposes, such as the prevention of metastasis to lymphatic systems after operation, or therapeutic treatment or extent of tumor regression. For example, in the case of the intraarterial administration the maximum dose can be 5 mg per every half month and in the case of the intravenous administration it is 1–3 mg per every half day. For local application as ointments or for oral administration, the dosage may be further increased.

The NCS derivatives (I) of the present invention may be stably dispersed in lipid contrast media of Lipiodol under ultrasonic wave and the like. When the dispersion of the NCS derivatives (I) is dispersed in Lipiodol prepared to contain 1–2 mg/1 ml in the suspension, it can be applied for intraarterial administration, and the Lipiodol containing the suspension derivative will stay in the tumor area selectively for a long period of time, as a result high antitumor activity is expected. Simultaneously the Lipiodol predominantly locate in the tumor will facilitate the determination of both the size and location of the tumor by X-ray.

The NCS derivatives (I) of the present invention show much stabler biological activity than that of NCS in lipid. Therefore, the NCS derivatives (I) of the present invention have the excellent activity in the above described intraarterial injection wherein a dose is limited.

The NCS derivatives (I) of the present invention is dissolved in 1–9% of aqueous sodium bicarbonate. When the solution is applied in intravenous administration, said medicine accumulates in lymphatic system resulting into antimetastatic effect therein. In the NCS derivatives (I) of the present invention, the half-life period of the biological activity in the whole blood is about 10–30 minutes, while that of NCS is about 2–3 minutes, so that it has been found in the following examples that the activity of the present invention may be maintained for far longer period of time than NCS and the retention of the antitumor activity which has been insufficient in NCS has been noticeably improved. Therefore, even in the above described intravenous injection, an excellent activity can be attained with improved chemotherapeutic effect.

In any route of administration the NCS derivatives (I) accumulate preferably at the tumor tissue. In the tumorous area, the NCS derivatives (I) directly separates NCS or is partially hydrolyzed to separate NCS to exert the antitumor activity, after which NCS portion and the partially half-estified styrene-maleic acid copolymeric portion are safely excreted out of the body in urine.

Thus, the NCS derivatives (I) of the present invention show very desirable activity as an anticancer agent.

The following examples are given for purpose of illustration of this invention and are not intended as limitations thereof.

EXAMPLE 1

(1) Polymerization of styrene-maleic anhydride copolymer:

30 l of cumene was charged into an explosion proof vessel of an inner volume of 150 l, to which a homogeneous solution consisting of 3.5 kg of maleic anhydride, 20 l of cumene, 3.7 kg of styrene, and 200 g of benzoyl peroxide were fed continuously in 65 minutes while being heated at 150° C. After the feeding, stirring was carried out at 150° C. for 60 minutes. Then, the reaction mixture was cooled to room temperature. Thereafter, 30 l of n-hexane was added thereto to precipitate the polymer formed. The liquid phase was taken out and the precipitated polymer was obtained. After the polymer was pulverized, it was washed with n-hexane, followed by drying. The yield of the thus obtained polymer was 7.3 kg. The number-average molecular weight ($\overline{Mn}$) of the polymer measured by vapor pressure osmometry (abbreviated as VPO hereinafter) was 1,680. It was confirmed according to the NMR spectrum measurement that the polymer thus obtained was a copolymer of styrene and maleic anhydride in a molar ratio of 1:1. (see FIG. 1).

(2) Fractionation of styrene-maleic anhydride copolymer:

40 g of the styrene-maleic anhydride copolymer (SMA) obtained in the step (1) was dissolved in 1.4 l of acetone, and 3.8 kg of glass beads (average particle size 0.1 mm) the surface of which had been treated beforehand with a coupling agent silane were added thereto. Thereafter, the acetone was evaporated to deposit SMA on the surfaces of the glass beads.

The SMA deposited glass beads and 1.4 l of a mixed solvent of acetone and n-hexane (the volume ratio thereof being 8:92 at 25° C.) were charged into a column having an inner diameter of 80 mm and a length of 80 cm, while keeping the temperature of the system at 25° C., then three kinds of mixed solvents of acetone and n-hexane [the mixed solvents at 25° C. being (i) 0.6 l of the mixed ratio of 8:92, (ii) 3.0 l of the mixed ratio of 22:78, and (iii) 3.0 l of the mixed ratio of 34:66 in this order] were successively fed, and the liquid was eluted from the lower outlet of the column. An eluate obtained when the mixed solvent of acetone and n-hexane with the volume ratio of 34:66 was concentrated and dried under reduced pressure to obtain 6.3 g of a sample. This sample was subjected to gel permeation chromatography (abbreviated as "GPC" hereinafter) and the weight average molecular weight ($\overline{Mw}$) was 1,350, the number-average molecular weight ($\overline{Mn}$) was 1,170 ($\overline{Mw}/\overline{Mn}=1.16$). According to the VPO method, the $\overline{Mn}$ was 1,170.

(3) Partial half n-butyl esterification of the fractionated SMA:

6.0 g of SMA obtained in the step (2), 1.95 g of n-butyl alcohol, 16 ml of dioxane and 0.06 g of lithium acetate were charged into a glass test tube, followed by sealing, and were homogeneously dissolved at room temperature under shaking for 24 hours. Then, this solution was kept at 90° C. for 17 hours and it was cooled to room temperature. Thereafter, the reaction liquid was taken out. The reaction liquid thus taken out was diluted two fold with dioxane and lyophilized, and then the product was dried under vacuum to obtain a light yellowish flake-like substance, which was pulverized to obtain 7.8 g of powder. The infrared absorption spectrum was measured by the KBr powder method, and it was confirmed through the optical densitites at wave number of 1,780 cm$^{-1}$ and 700 cm$^{-1}$ that the powder thus obtained was partially half n-butyl esterified styrene-maleic anhydride copolymer (abbreviated as "Bu-SMA" hereinafter) wherein the content of the remaining maleic anhydride ring is 30.5 mol% (the maleic anhydride ring contained in one molecule being 1.7). According to GPC, $\overline{Mw}$ was 1,480, $\overline{Mn}$ was 1,290 and $\overline{Mw}/\overline{Mn}$ was 1.15.

(4) Reaction of NCS with Bu-SMA:

0.20 g of neocarzinostatin (NCS) was dissolved in 5.0 ml of 0.8M aqueous solution of sodium bicarbonate under ice-cooling in the dark. The powdery Bu-SMA was stepwise added in a total amount of 1.02 g thereto in several times. Thus, the reaction was carried out for 97 hours while the pH of the solution being kept around 8.5 to obtain the conversion of the primary amino group of NCS of 97.5 mol%. The conversion of such a primary amino group can be determined by a method (hereinafter referred to as "TNBS" method) in which a small amount of a sample taken out from the reaction liquid was diluted, and was reacted with trinitrobenzene sulfonic acid to produce a nitrobenzene derivative, which was determined based on the amount of the primary amino group spectrophotometrically by a visible absorption spectrometer at 420 nm.

The thus obtained reaction mixture was transferred to a dialysis tube (Union Carbide Co., Ltd., U.S.A.) having a cut-off molecular weight of 8,000, and dialyzed for three days against aqueous 5 mM ammonium bicarbonate under ice-cooling in the dark while the exterior liquid was exchanged sometimes.

A part of the partially purified solution was diluted with 10 mM of aqueous ammonium bicarbonate to obtain pH of 7.9. FIG. 2 shows GPC curves depicted by using a G-3000 SW column manufactured by Toyo Soda Co., Ltd. The peaks at the retention time 16 minutes as mentioned at wavelengths 254 and 280 nm have maxima nearly equal to each other and thus they are assigned to the derivatives (I), while the absorption of the retention time of 19 minutes for 254 nm only is assigned to the hydrolyzed and ring-opened product of Bu-SMA.

(5) Purification of the NCS derivatives (I):

A half amount of the dialyzed reaction liquid was poured into a column having an inner diameter of 50 mm and a length of 60 cm (K 50/60, Pharmacia Fine Chemicals AB, Uppsala, Sweden) packed with Sephadex G-75, and elution was carried out at a flow rate of 6.0 ml/min at 10° C. in the dark by using 5 mM aqueous ammonium bicarbonate. Absorption of the eluate was continuously monitored at the wavelength of 254 nm (FIG. 3). The eluate cut from 60 to 100 minutes after the sample injection was then lyophilized. This operation was repeatedly done under the same conditions. The purified NCS derivatives (I) thus obtained weighed 186 mg in total.

When the electrophoresis was performed by using polyacryl amide gel containing dodecyl sodium sulfate, the NCS derivative thus obtained showed a single spot. As shown in FIG. 4a, the GPC measured at pH 7.9 by using a G-3000 SW column manufactured by Toyo Soda Co., Ltd. with a mobile phase of 10 mM aqueous ammonium bicarbonate indicated a sharp peak.

The elementary analysis showed N: 11.43% by weight, C: 51.99% by weight, and H: 6.32% by weight.

The average molecular weight of the NCS derivative based on the content of the nitrogen is 13,300. The average molecular weight was calculated according to the following formula (X):

$$\overline{Md} = M_N \cdot N_N / N_d \quad (X)$$

wherein $\overline{Md}$ is the average molecular weight of the NCS derivative, $M_N$ is the molecular weight of NCS (=10,700), $N_N$ is the nitrogen content according to the elementary analysis of NCS and 14.24% by weight, $N_d$ is the nitrogen content (% by weight) according to the elementary analysis of the NCS derivative. Meanwhile, the average molecular weight of NCS derivative shown in the formula (I) is 10,700+1,480×2=13,660 based on the weight-average molecular weight of E-SMA of 1,480 of E-SMA obtained room the GPC. Since the above mentioned average molecular weight based on the nitrogen content is in agreement with this value, it can be understood that in NCS derivative obtained in this Example, two residues of partially half-esterified styrene-maleic acid copolymeric residues are bonded to one NCS residue as shown by the formula (I). The average molecular weight ($\overline{Mr}$) of the partially half-esterified styrene-maleic acid copolymeric residue portion contained in the NCS derivative is determined from the average molecular weight ($\overline{Md}$) of NCS derivatives thus determined according to the following formula (XI):

$$\overline{Mr} = (\overline{Md} - M_N)/2 \qquad (XI)$$

wherein $\overline{Mr}$ denotes the average molecular weight of the partially half-esterified styrene-maleic acid copolymeric residue in the NCS derivative, $\overline{Md}$ is the average molecular weight of the NCS derivative, and $M_N$ is the molecular weight of NCS, (=10,700). According to this formula, $\overline{Mr}$ is 1,300. This value is not largely different from the weight-average molecular weight of the starting material of E-SMA being 1,480 obtained from GPC.

Although the melting point measurement was tried, no clear melting point was observed.

Figure 6A:
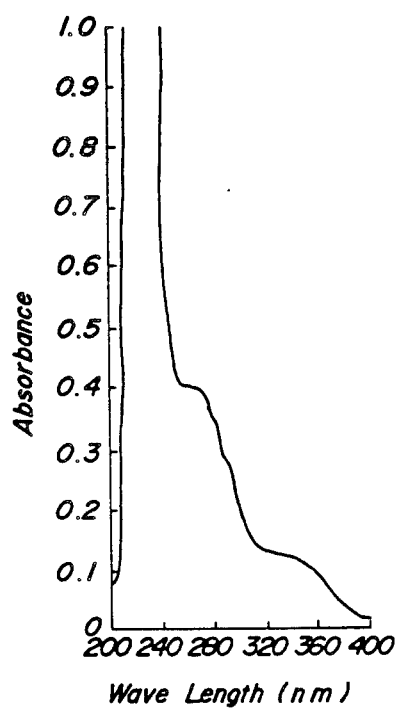
FIGS. 6a, 6b and 6c are examples of ultraviolet (UV) spectra of the NCS derivatives according to the present invention.

FIG. 5a shows an infrared absorption spectrum in a KBr tablet method (hereinafter abbreviated as "IR spectrum") and FIG. 6a shows ultraviolet-visible absorption spectrum (hereinafter abbreviated as "UV spectrum") in a 0.5 mM aqueous ammonium bicarbonate. These spectra support the structure of the NCS derivative of the formula (I) according to the present invention.

EXAMPLE 2

The fractionated SMA of $\overline{Mw}$ 1,480 and $\overline{Mn}$ 1,230 ($\overline{Mw}/\overline{Mn}$ 1.20) was prepared in the similar manner as the Example 1 except that a mixed solution of acetone and n-hexane of 38:62 was used as the third mixed liquid of acetone and n-hexane in fractionating SMA obtained in the Example 1(1). 4.0 g of the fractionated SMA was esterified under the same conditions as in Example 1(3) except that 0.80 g of ethanol, 12 ml of dioxane, and 40 mg of lithium acetate were employed, whereby 4.9 g of a partially half ethyl-esterified maleic anhydride copolymer (hereinafter abbreviated as "Et-SMA") having an anhydride ring content of 24.0 mol% (the anhydride ring 1.6 per molecule on the average), $\overline{Mw}=1,580$ and $\overline{Mn}=1,340$ ($\overline{Mw}/\overline{Mn}=1.18$) was obtained.

Similar to Example 1(4), 0.2 g of NCS was dissolved in 5.0 ml of 0.8M aqueous solution of sodium bicarbonate, and 1.2 g of Et-SMA was stepwise added thereto in several times. In this reaction, the pH of the solution was kept around 8.5. Twenty seven hours after the initial addition, the conversion of the primary amino group was 97.5 mol%. Immediately thereafter, the reaction liquid was dialyzed and 38 ml of the dialyzate was subjected to a gel filtration. Then, the filtrate was lyophilized to obtain 148 mg of the purified NCS derivative (I).

Figure 4B:
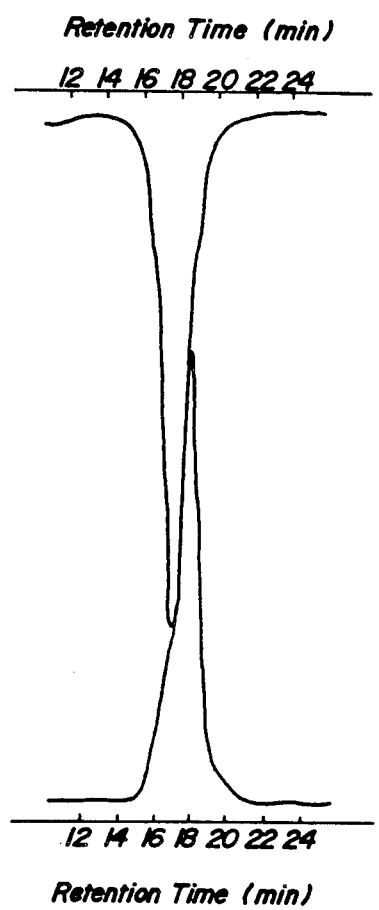
Figure 6B:
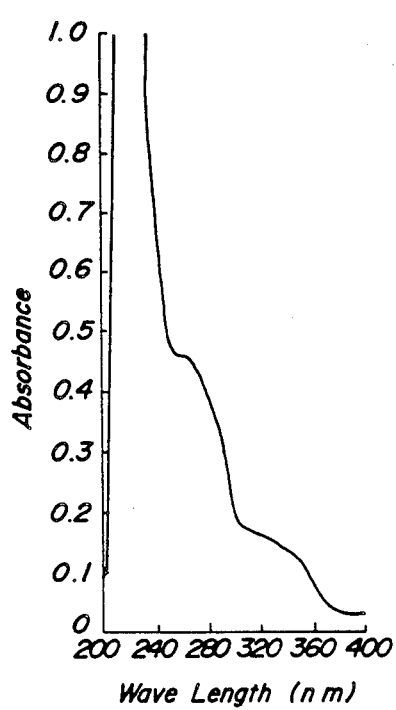

The NCS derivative thus obtained indicated a single spot in the electrophoresis. The GPC is shown in FIG. 4b. The elementary analysis values were N: 10.74% by weight, C: 52.90% by weight, and H: 6.18% by weight. The average molecular weight based on these data was 14,200, and the average molecular weight of the partially half ethyl-esterified styrene maleic acid copolymeric residue was 1,750. The IR spectrum and the UV spectrum are shown in FIG. 5b and FIG. 6b. From these data, the structure of NCS derivative according to the present invention shown by the formula (I) was confirmed.

EXAMPLE 3

The SMA produced in Example 1(1) was fractionated by the method described in Example 1(2) except that the volume fraction of acetone in the second and third mixed liquids of acetone-n-hexane mixture were 23% and 37%, respectively, to obtain 9.1 g of a fractionated SMA of $\overline{Mw}=1,480$, $\overline{Mn}=1,250$ ($\overline{Mn}=1,230$ in the VPO method) and $\overline{Mw}/\overline{Mn}=1.18$. 4.0 g of the fractionated SMA thus obtained was reacted as in the case of Example 1(3) by using 1.60 g of ethyl cellosolve as alcohol, and 0.04 g of lithium acetate to obtain 4.9 g of a partially half 2-ethoxyethyl-esterified styrene maleic anhydride copolymer (hereinafter abbreviated as "Et-Cell-SMA") having an anhydride ring content of 25.4 mol% (the anhydride ring being 1.6 per molecule on the average), $\overline{Mw}=1,700$ and $\overline{Mn}=1,440$ ($\overline{Mw}/\overline{Mn}=1.19$).

Similar to Example 1(4), the Et-Cell-SMA was added and dissolved stepwise in a total amount of 1.3 g into 5.0 ml of 0.8M aqueous solution of sodium bicarbonate in which 0.2 g of the NCS has been dissolved. While keeping the pH of the solution at about 8.5, the reaction was performed. After 98 hours of incipience of Et-Cell-SMA addition, the conversion of the amino group was 97.6 mol%. The reaction mixture thus obtained was subjected to dialysis, gel filtration and lyophilization to obtain 189 mg of the purified NCS derivative (I).

Figure 6C:
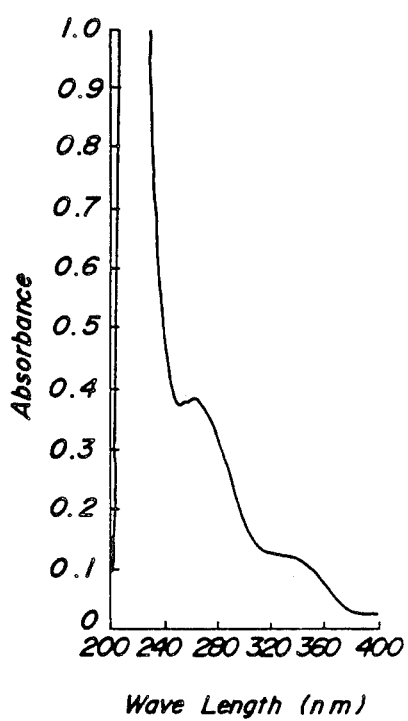
Figure 6D:
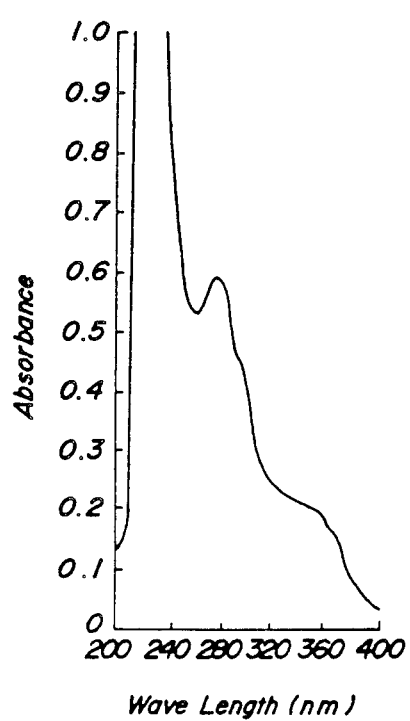
FIG. 6d is an example of UV spectra of NCS which is a starting material of the NCS derivatives according to the present invention.

Thus obtained NCS derivative showed a single spot in the electrophoresis. The GPC is shown in FIG. 4c. The elementary analysis data were N: 10.72% by weight, C: 53.49% by weight, and H: 6.38% by weight. The average molecular weight based on these data was 14,200, and the average molecular weight of the partially half 2-ethoxyethyl-esterified styrene-maleic acid copolymeric residue was 1,750. The IR spectrum and the UV spectrum were shown in FIG. 5c and FIG. 6c, respectively. From these data, the structure of NCS derivative of the formula (I) according to the present invention was confirmed.

EXAMPLE 4

6.0 g of the factionated SMA obtained in Example 2 was partially half-esterified by using 1.60 g of n-butyl alcohol, 16 ml of dioxane and 0.06 g of lithium acetate to obtain 6.3 g of Bu-SMA having an anhydride ring content of 44.4 mol% (the anhydride ring being 2.8 per molecule on the average. $\overline{Mw}$ was 1,660 and $\overline{Mn}$ was 1,390 ($\overline{Mw}/\overline{Mn}=1.18$). Bu-SMA thus obtained was reacted for 70 hours as in the case of Example 1(4) to obtain the conversion of the primary amine in NCS of 99.3 mol%. The product was subjected to the dialysis, gel filtration, and lyophilization to obtain 182 mg of the purified NCS derivative (I). The elementary analysis data were N: 10.67% by weight, C: 52.06% by weight and H: 6.22% by weight. The average molecular weight was 14,300, and the average molecular weight of the partially half n-butyl-esterified styrene maleic acid copolymeric residue was 1,800.

EXAMPLE 5

The fractionated SMA was partially half methyl-esterified with methanol to obtain a partially half methyl-esterified styrene-maleic anhydride copolymer (hereinafter abbreviated as Me-SMA) having the anhydride ring content of 25.0 mol% (the anhydride ring content being 1.7 per molecule on the average) $\overline{M}w=1,510$ and $\overline{M}n=1,280$ ($\overline{M}w/\overline{M}n=1.18$). Me-SMA thus obtained was reacted with NCS and then purified similarly to Example 2, and the corresponding NCS derivative (I) was isolated. The elementary analysis data were N: 10.87% by weight, C: 52.81% by weight, and H: 6.11% by weight. The average molecular weight was 14,000 and in which the average molecular weight of the partially half methyl-esterified styrene maleic acid copolymeric residue portion was 1,650.

EXAMPLE 6

The fractionated SMA was partially esterified with 1,3-diethoxy-2-propanol to obtain partially half 1-(ethoxymethyl)-2-ethoxyethyl-esterified styrene maleic anhydride copolymer having an anhydride ring content of 25.3 mol% (the anhydride ring being 1.6 on the average), $\overline{M}w=1,960$, $\overline{M}n=1,650$ ($\overline{M}w/\overline{M}n=1.19$). The thus obtained copolymer was reacted with NCS and then purified as in the case of Example 3 to isolate the corresponding NCS derivative (I). The elementary analysis data were N: 10.25% by weight, C: 53.58% by weight, H: 6.51% by weight. The average molecular weight was 14,900 and that of the partially half 1-(ethoxymethyl)-2-ethoxyethyl-esterified styrene-maleic acid copolymeric residue portion

EXAMPLE 7

NCS derivative (I) was produced according to the following manner by using Bu-SMA ($\overline{M}w$ 1,620, $\overline{M}w/\overline{M}n$ 1.10) which had been prepared in the same conditions as in Example 1(1)–(3) except that dicumyl peroxide was used as a polymerization catalyst instead of benzoyl peroxide.

After 0.67 g of NCS was dissolved in 20 ml of 0.8M aqueous sodium bicarbonate under ice-cooling in the dark, Bu-SMA was added stepwise in a total amount of 8.00 g under stirring in several times, and the reaction was carried out for 50 hours while the pH was kept higher than 8.3. The conversion of the primary amino group of the NCS was 97.8 mol%.

The reaction mixture obtained was diluted with water to 90 ml, which was poured into a column having an inner diameter of 50 mm and a length of 90 cm packed with a Sephadex G-75 (Pharmacis Fine Chemicals AB, Uppsala, Sweden). Elution was carried out at a flow rate of 4.0 ml/min in the dark at 5° C. by using 5 mM aqueous ammonium bicarbonate as a carrier solvent. Similar to Example 1, while the absorbance of the eluate was monitored at a wavelength of 254 nm, the eluate cut from 1⅔ hour to 6⅔ hours after the sample injection was collected. The volume of this fraction was 1,050 ml. This was concentrated to 60 ml by using an ultra filtering membrane SM 14539 (Sartorius BmgH, West Germany; cut-off molecular weight of 10,000).

One half of the concentrated fraction liquid, that is, 30 ml, was applied to a column with 50 mm in diameter and 60 cm in length, which had been packed with Bio-Gel P-60 (Bio-Rad Laboratories, U.S.A.) and elution was carried out (Bio-Rad Laboratories, U.S.A.) and elution was carried out at a flow rate of 1.2 ml/min in the dark by using 5 mM aqueous ammonium bicarbonate. Similar to the above, the eluate from 12¾ hours to 16 1/12 hours after the sample injection was collected, and the concentration was carried out by using the same ultrafiltration membrane as described above, followed by the lyophilization. The yield of the purified NCS derivatives (I) was 266.5 mg.

The elementary analysis data of the derivative thus obtained were N: 11.31% by weight, C: 52.97% by weight and H: 6.40% by weight. The average molecular weight was 13,470, and that of the partially half butyl-esterified styrene maleic acid copolymeric residue portion was 1.385.

EXAMPLE 8

The biological activity defined above was measured for each of the NCS derivatives obtained in Examples 1–3. Twenty μl aliquots of the NCS derivative having various concentrations were added to a paper disc of 8 mm in diameter which had been placed on the agar plate with culture medium (Müller-Hinton) preinoculated with Sarcina lutea PCI 1001 strain. After allowing an adequate diffusion time (5 hours) at 4° C., the cultivation was resumed out at 37° C. for 12 hours. Thereby, the concentration of the diluted solution required to give an inhibition diameter of 13 mm was determined and such an effective concentration in NCS was defined to be "1" and the concentrations of NCS derivatives thus determined were shown by the relative value based on the value 1 of NCS and the relative values obtained were taken as the index of the biological activity.

As to the acute toxicity in mice, the diluted solution was administered once intravenously into the tail of male ICR mice (one group: 6 mice) of 5~6 week old and then said mice were observed for 14 days to determine $LD_{50}$.

The data on the lutea biological assay and the acute toxicity are shown in Table 1. It is seen that the NCS derivatives according to the present invention have the biological activity comparable to that of NCS but the acute toxicity of the former are greatly lowered.

FIG. 7 shows an inactivation curve obtained by the measurement of the residual lutea biological activity of the NCS derivative (I) while being incubated at the concentration of 100 μg/ml in a fresh human blood at 37° C. From this figure, the half-time as determined by the biological activity in the whole blood were 32 minutes and 8 minutes in NCS derivatives in Examples 1 and 3 respectively. The half-time for NCS used as control is 2–3 minutes. Therefore, it is clear that the NCS derivatives according to the present invention are much better in the stability of the activity in the whole blood or serum than the parental NCS.

Further, the antitumor activity against Ehrlich's carcinoma (solid type) was determined by using NCS derivative of Example 1. Results are shown in Table 2. The NCS derivative according to the present invention has an antitumor activity equivalent to NCS.

TABLE 1

| Item | Biological assay[1] (Relative value) | Acute toxicity ($LD_{50}$) mg/kg |
|---|---|---|
| Example 1 | 1.41 | 4.63 |
| Example 2 | 1.29 | 5.54 |
| Example 3 | 1.24 | — |

TABLE 1-continued

| Item | Biological assay[1] (Relative value) | Acute toxicity (LD$_{50}$) mg/kg |
|---|---|---|
| Control NCS | 1 (control) | 1.33 |

Note:
[1]*Sarcina lutea* PCI-1001 strain was used. The concentration at which the inhibition zone becomes 13 mm in diameter on the agar plate was indicated by a relative value taking that of NCS as standard.

TABLE 2

| | Dosage (mg/kg) | Tumor-inhibiting rate (%) | Survival rate (number of survival mice/number of tested mice) |
|---|---|---|---|
| Example 1 | 2.0 | — | 0/8 |
| NCS derivative | 1.0 | 56.2 | 2/8 |
| | 0.5 | 40.5 | 7/8 |
| | 0.25 | 31.1 | 8/8 |
| | 0.125 | 7.4 | 8/8 |
| NCS | 0.4 | 41.0 | 3/8 |
| | 0.2 | 34.8 | 7/8 |
| | 0.1 | 16.9 | 8/8 |
| | 0.05 | 3.6 | 8/8 |

Tumor: Ehrlich's carcinoma (solid type)
Inoculated cell number: $5 \times 10^6$/mouse (subcutaneous)
Mouse: ddY, ♂, five weeks old
Administration: intraperitoneal administration. Once daily (total 5 times) 1st day, 2nd day, 4th day, 5th day and 6th day after the tumor was transplanted).
Evaluation: Tumor-inhibiting rate(%) = (C− T) × 100/C
C: The average tumor size (mm$^2$) of the control group,
T: The average tumor size (mm$^2$) of the treated group.
Evaluation on the tumor-inhibiting rate was made on the made 2nd week after transplantation of the tumor,
Survival rate: judged on the 4th week after transplantation of the tumor.

COMPARATIVE EXAMPLE 1

10 g of unfractionate styrene-maleic anhydride copolymer having $\overline{Mw}=3,520$, $\overline{Mn}=1,830$ ($\overline{Mw}/\overline{Mn}=1.92$), 0.1 g of lithium acetate, 2.8 g of n-butyl alcohol and 25 ml of dioxane were charged into a test tube, and after the top portion thereof was sealed by fusion, the test tube was shaken at room temperature for 24 hours to obtain a homogeneous solution. The resulting solution was heated at 90° C. for 15 hours and then cooled to room temperature. Then, the reaction mixture was taken out of the test tube, and diluted to about two fold with dioxane, followed by lyophilization and lyophilized to obtain a light yellowish flake-like Bu-SMA. This Bu-SMA had $\overline{Mw}$ of 4,490 and $\overline{Mn}$ of 2,280 ($\overline{Mw}/\overline{Mn}=1.96$), and the content of remaining maleic anhydride residue was 28 mol% (the anhydride ring per one molecule being 2.8 on the average).

0.5g of NCS was dissolved in 50 ml of 0.5M aqueous sodium bicarbonate under ice-cooling in the dark. Then, 3.0 g of powdery Bu-SMA was added stepwise thereto while stirring and the mixture was thoroughly stirred until the powder was completely dissolved. The reaction mixture was left to stand at 4°–6° C. for 16 hours after the complete dissolution of finally added Bu-SMA. The conversion of the primary amino group of NCS reached 71.7 mol%. The pH of the reaction system was kept between 8.3 and 8.7 during the stirring. Thereafter, the reaction mixture was transferred to a dialysis tubing and dialyzed at 4°–6° C. under pressurized conditions against 1 l of 10 mM aqueous ammonium bicarbonate for three days while the dialyzing liquid was replaced several times. The reacton mixture after dialysis was lyophilized to obtain white fluffy NCS composite represented by the formula (III). The elementary analysis data were N: 3.42% by weight, C: 60.51% by weight, H: 6.36% by weight. The apparent average molecular weight obtained from the nitrogen content according to the formula (X) was about 44,600. The partially half n-butyl-esterified styrene-maleic acid polymeric residue forming the composite with respect to 1 mole of NCS residue was about 7 mole on the average. The lutea biological activity of the NCS composite was determined according to the method described in Example 8, and it has been found that while the value of NCS is 1, that of NCS composite of this Control Example is 18.0. Thus, the NCS composite has a far lower lutea biological activity as compared with the NCS derivative (I) of the present invention.

COMPARATIVE EXAMPLE 2

Figure 8:
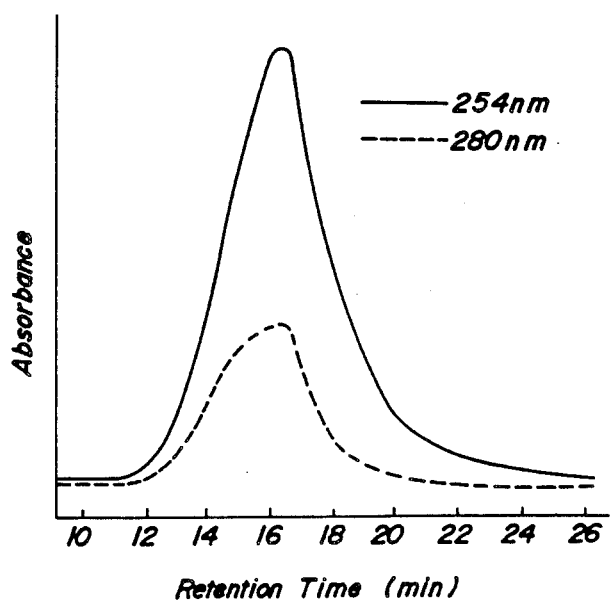
FIG. 8 is an example of GPC of a solution obtained through dialysis after the reaction of E-SMA having a wide molecular weight distribution with NCS.

SMA used in the Comparative Example 1 was partially half n-butyl-esterified without being fractionated to obtain Bu-SMA of an anhydride ring content of 29.8 mol%, (the average content of anhydride ring per molecule being 2.9), $\overline{Mw}$ of 4,470, and $\overline{Mn}$ of 2,280 ($\overline{Mw}/\overline{Mn}=1.96$). Similar to Example 1(4), the Bu-SMA was reacted with NCS, so that the conversion of the primary amino group in the NCS reached 99.6 mol%. FIG. 8 shows the GPC trace of the roughly purified solution obtained by dialyzing the reaction liquid. This GPC trace of the solution is a curve of broader width as compared with GCP of the Example 1 (FIG. 2), and the ratio between the absorbance ($h_{280}$) at 280 nm and the absorbance ($h_{254}$) at 254 nm, $h_{280}/h_{254}$, is as low as 0.36 (in FIG. 2 of Example 1, $h_{280}/h_{254}=0.90$). Thus, it is seen that the peak of NCS derivative overlaps with that of the hydrolyzed and ring-opened product of Bu-SMA. As apparent from this GPC profile, when the Bu-SMA which has a high weight average molecular weight with a wider molecular weight distribution is used, the resulting NCS derivative cannot be isolated by gel filtration from the reaction solution.

What is claimed is:

1. A substantially pure neocarzinostatin derivative having the formula (A):

(SMA)—(NCS)—(SMA)    (A)

wherein (NCS) is a divalent neocarzinostatin residue and (SMA) comprises the monovalent residue of a partially half-esterified styrene-maleic acid copolymer having a weight-average molecular weight of from 800 to 2,500, said (NCS) residue being bonded to said (SMA) residues via amide linkages formed between primary amino groups of the neocarzinostatin molecule and carbonyl groups of the partially half-esterified styrene-maleic acid copolymer.

2. The neocarzinostatin derivative as defined by claim 1, said styrene-maleic acid copolymer comprising (a) styrene residues, (b) half-esterified maleic acid residues, (c) maleic acid residues and (d) residues of the formula:

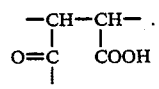

3. The neocarzinostatin derivative as defined by claim 2, said half-esterified maleic acid residues (b) having the formula:

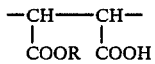

wherein R is lower alkyl, mono-lower alkyloxyethyl or glyceryl di-lower alkyl ether.

4. The neocarzinostatin derivative as defined by claim 3, wherein R is n-butyl.

5. The neocarzinostatin derivative as defined by claim 2, wherein the molar ratio of the residues (a) to the sum of the residues (b), (c) and (d) ranges from about 1:1 to 1.3:1.

6. The neocarzinostatin derivative as defined by claim 5, wherein the molar ratio of the residues (a) to the sum of the residues (b), (c) and (d) is about 1:1.

7. The neocarzinostatin derivative as defined by claim 2, said primary amino groups of the neocarzinostatin molecule comprising the alanine residue at the N-terminal and the lysine residue at the 20th position thereof.

8. The neocarzinostatin derivative as defined by claim 2, wherein the molar ratio of the residues (b) to the sum of the residues (b), (c) and (d) ranges from 35 to 85 mol %.

9. A process for the preparation of a neocarzinostatin derivative, comprising reacting neocarzinostatin, in an aqueous reaction medium, with a molar excess of a partially half-esterified styrene-maleic anhydride copolymer, said copolymer satisfying the formulae (B) and (C):

$$800 \leqq \overline{M}w \leqq 2,500 \qquad (B)$$

$$\overline{M}w/\overline{M}n \leqq 1.5 - 1.1 \times 10^{-4}\, \overline{M}w \qquad (C)$$

wherein $\overline{M}w$ is the weight-average and $\overline{M}n$ the number-average molecular weight thereof.

10. The process as defined by claim 9, further comprising isolating the neocarzinostatin derivative of claim 1 from the reaction product thereof.

11. The process as defined by claim 10, said isolating being by gel filtration.

12. The process as defined by claim 10, comprising reacting 2 to 15 parts by weight of said copolymer with 1 part by weight of the neocarzinostatin.

13. The process as defined by claim 12, wherein the concentration of the total amount of the neocarzinostatin and the copolymer in said reaction medium ranges from 10 to 35% by weight.

14. The process as defined by claim 13, wherein the pH of the reaction medium ranges from 7.5 to 9.5.

15. The process as defined by claim 14, wherein the reaction is carried out at a temperature of less than 15° C. under dark conditions.

16. The process as defined by claim 11, wherein prior to said gel filtration, the reaction product is preliminarily purified.

17. The process as defined by claim 11, wherein said gel filtration is carried out utilizing a substrate having an exclusion limit of 50,000 to 150,000, with globular proteins as the molecular weight standard.

18. The process as defined by claim 9, wherein said reactant copolymer is in powder form.

19. A composition of matter comprising the neocarzinostatin derivative as defined by claim 1, and a pharmaceutically acceptable carrier therefor.

20. The composition of matter as defined by claim 19, comprising a pharmaceutically acceptable lipid carrier therefor.

21. The composition of matter as defined by claim 19, comprising a pharmaceutically acceptable aqueous carrier therefor.

22. The composition of matter as defined by claim 19, further comprising an X-ray contrast medium.

23. A method for the treatment of cancer in a mammalian organism in need of such treatment, comprising administering thereto an anticancer effective amount of the neocarzinostatin derivative as defined by claim 1.

24. A method for the treatment of cancer in a mammalian organism in need of such treatment, comprising administering thereto an anticancer effective amount of the composition of matter as defined by claim 19.

* * * * *